(12) United States Patent
Langford et al.

(10) Patent No.: US 7,845,346 B2
(45) Date of Patent: Dec. 7, 2010

(54) SPRAY DEVICE

(75) Inventors: Alan Langford, Hoddesdon (GB);
Brian Barney, Great Dunmow (GB);
Caroline Stretton, Hamilton (GB)

(73) Assignee: Norton Healthcare Ltd., London (GB)

( * ) Notice: Subject to any disclaimer, the term of this patent is extended or adjusted under 35 U.S.C. 154(b) by 0 days.

(21) Appl. No.: 10/344,789

(22) PCT Filed: Aug. 15, 2001

(86) PCT No.: PCT/GB01/03648

§ 371 (c)(1),
(2), (4) Date: Dec. 3, 2003

(87) PCT Pub. No.: WO02/16235

PCT Pub. Date: Feb. 28, 2002

(65) Prior Publication Data

US 2005/0121024 A1 Jun. 9, 2005

(30) Foreign Application Priority Data

Aug. 18, 2000 (GB) .................................. 0020296.0

(51) Int. Cl.
*A61M 11/00* (2006.01)
(52) U.S. Cl. .............................. 128/200.23; 128/200.14
(58) Field of Classification Search ............ 128/200.14, 128/200.16, 200.23, 203.15, 200.19, 20.23, 128/200.18, 203.21
See application file for complete search history.

(56) References Cited

U.S. PATENT DOCUMENTS

| | | | | | |
|---|---|---|---|---|---|
| 3,361,306 | A | * | 1/1968 | Wayne | 222/402.13 |
| 3,368,591 | A | * | 2/1968 | Zerbetto | 141/20 |
| 3,505,870 | A | * | 4/1970 | Smylie | 73/323 |
| 3,865,279 | A | * | 2/1975 | James | 222/182 |
| 4,119,096 | A | * | 10/1978 | Drews | 128/200.16 |
| 4,358,483 | A | * | 11/1982 | Waugh | 427/287 |
| 5,060,823 | A | * | 10/1991 | Perlman | 222/1 |
| 5,134,993 | A | * | 8/1992 | van der Linden et al. | 128/200.14 |
| 5,775,321 | A | * | 7/1998 | Alband | 128/200.23 |
| 6,142,339 | A | * | 11/2000 | Blacker et al. | 222/23 |
| 6,955,169 | B2 | * | 10/2005 | Khan | 128/200.22 |

FOREIGN PATENT DOCUMENTS

| | | |
|---|---|---|
| GB | 2195544 | 4/1988 |
| JP | 4-044946 U | 4/1992 |
| JP | 4-112027 U | 4/1992 |
| JP | 10-081336 U | 3/1998 |
| WO | WO 9632345 A1 * | 10/1996 |

* cited by examiner

*Primary Examiner*—Darwin P Erezo
(74) *Attorney, Agent, or Firm*—RatnerPrestia

(57) ABSTRACT

The present invention relates to a spray device (e.g., an inhaler) comprising an aerosol formulation administered to the respiratory or nasal tract in which the level of formulation remaining in the device can be readily inspected. The device comprises a glass vial (1) coated with a coating of polymeric material having at least one clear or translucent portion (4).

33 Claims, 4 Drawing Sheets

SPRAY DEVICE

FIELD OF THE INVENTION

The present invention relates to a respiratory aid adapted to combat more reliably the symptoms of a subject with a respiratory disorder, in particular to a spray device (e.g., an inhaler) comprising an aerosol formulation administered to the respiratory or nasal tract.

BACKGROUND OF THE INVENTION

Various respiratory aids are now widely available to a subject wishing to self-administer therapeutic and preventative agents to combat the symptoms of a respiratory disorder such as asthma. These aids come in a range of shapes and sizes to suit the age and ability of the subject. Such respiratory aids include inhalers and auxiliary devices such as spacers, optimisation chambers, reservoirs, expansion chambers and deceleration chambers.

A common example of a respiratory aid is the inhaler which is a manually operated device used to dispense into the respiratory passages a discrete amount of a therapeutic or preventative agent (e.g., in the form of a spray). One of the benefits of an inhaler is that the subject is able to manage the respiratory disorder through self-administration of a preventative agent. A successful preventative regime relies on regular self-administration of the preventative agent to avert breathing difficulties and other respiratory symptoms. Breathing difficulties may occur suddenly and indiscriminately and their onset frequently leads to a loss in co-ordination. A second benefit of an inhaler is that sudden respiratory attacks may be treated by immediate self-administration of the desired therapeutic agent. The preventative and therapeutic benefits of the inhaler rely on the subject being able to locate reliably and effortlessly an inhaler with an at least partially charged container.

In principle inhalers are available in two types, namely an aerosol device powered by a propellant (e.g., a metered dose inhaler of the type described in inter alia GB-A-2293110) or a powder containing device (e.g., a metered dose powder inhaler). The therapeutic or preventative agent may be in dry powder or liquid (e.g., suspension) form and generally speaking is drawn into the respiratory passages by simultaneously dispensing the agent and taking a sharp intake of breath.

Most forms of aerosol inhaler comprise a metal container for the therapeutic or preventative agent and a discharge valve through which the agent may be dispensed continuously or discretely via a nozzle. For example, conventional metered dose inhalers comprise a metal canister secured to a metered dose valve. A determination of the number of doses remaining in the canister requires a manual record of the number of doses which have been dispensed (for example using a mechanical counter). Many counter devices of a mechanical type have been proposed.

U.S. Pat. No. 3,505,870 discloses a metal aerosol container with a transparent window in a small circular opening in the base.

BRIEF SUMMARY OF THE INVENTION

The present invention is based on the recognition that the welfare of a subject having a respiratory disorder (such as asthma) may be improved by assisting them to rapidly and reliably assess the status of the container. More particularly, the present invention relates to a respiratory aid such as an inhaler adapted so that the subject may rapidly determine how much of the preventative or therapeutic agent remains within the container.

Thus viewed from one aspect the present invention provides a respiratory aid (e.g., a medical aerosol device) for use in self-administration of an agent for combating (e.g., preventing or treating) the symptoms of a respiratory disorder, said respiratory aid comprising:
  a container for the agent operatively connected to a discharge valve through which a therapeutically or preventatively effective amount of said agent may be dispensed via a nozzle and an actuator body adapted to actuate the valve, wherein the container comprises:
  a glass vial coated with a coating of polymeric material, the coating of polymeric material having at least one clear or translucent portion arranged to permit observation of the level of agent in the container.

Viewed from a further aspect the present invention provides a medical aerosol device comprises a container and a discharge valve through which fluid may be dispensed via a nozzle, an actuator adapted to actuate the valve, the container comprising a glass vial coated with a layer of polymeric material, the polymeric material having at least one clear or translucent portion arranged to permit observation of the level of liquid in the container.

DETAILED DESCRIPTION

The respiratory aid may be any type of inhaler including one of the group consisting of a pressurised metered dose inhaler (both manually operable and breath actuated), an aerosol inhaler and a dry powder inhaler.

Preferably the actuator is adapted to directly or indirectly administer a therapeutically or preventatively effective amount of said agent into the respiratory passages of a subject through a delivery outlet, said delivery outlet being adapted to fit in the subject's mouth or nose or into an auxiliary device (such as a spacer or an optimisation chamber).

Glass vials have not previously been used for medical aerosol devices because of the risk of breakage if the device is dropped, a risk which is increased in distressed subjects suffering from an asthma attack. Not only are the shards of glass hazardous but the patient may not have a replacement device readily to hand. Thus the use of glass in accordance with the invention is somewhat contrary to conventional wisdom. Application of a polymeric coating may advantageously reduce the risk of injury and distress in the event of breakage.

The polymeric coating may be composed of a polyolefin such as polyethylene, polypropylene, polystyrene or copolymers or blends thereof. Alternative polymers include ABS, acetyl, acrylic and other polymers. Polypropylene is preferred.

In a first embodiment the clear or translucent portion may comprise a window of reduced thickness of polymer coating. The window may be formed by polishing the portion of reduced thickness or by polishing the polymer coating to form a polished portion of reduced thickness.

Alternatively the clear or translucent portion may comprise a portion of increased thickness, the portion being polished to provide a transparent or translucent surface.

Two windows may be provided on opposite sides of the vial to advantageously facilitate transmission of light.

In a preferred embodiment, the clear or translucent portion extends axially of the vial. Gradations or other markings may be provided on or adjacent to the window to indicate the number of doses available.

The device is preferably a metered dose inhaler device or nasal spray.

The container may comprise a conventional metered dose inhaler or nasal spray casing, a window being provided to facilitate observation of the liquid level within the vial. Gradations or other markings may be provided on the casing in addition to or instead of markings on the vial.

The invention is further described by means of example, but not in any limitative sense with reference to the accompanying drawings.

Figure 2:
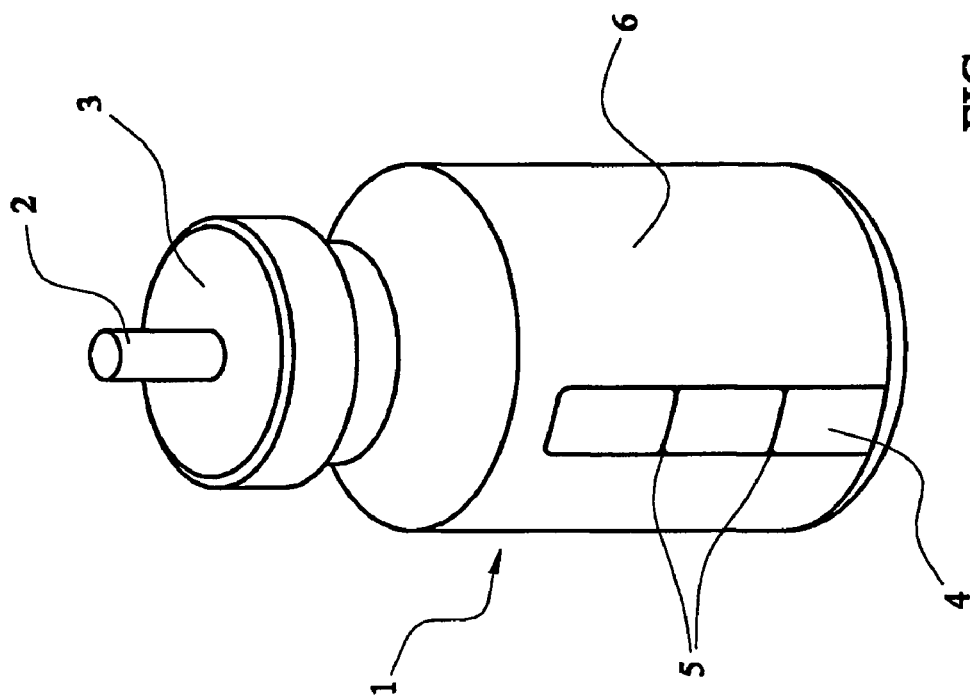
FIG. 2 is a perspective view of the vial shown in FIG. 1.
Figure 1:
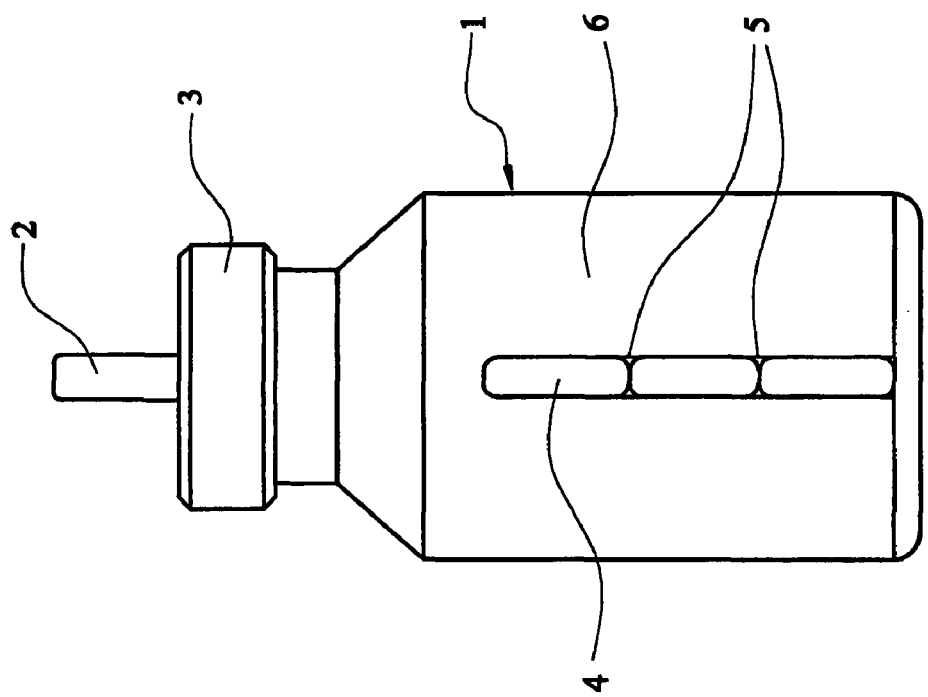
FIG. 1 is an elevational view of a vial in accordance with the invention.

FIGS. 1 and 2 illustrate a vial in accordance with an embodiment of this invention. The vial includes a body portion 23 having a side wall 25 and a neck portion 24 disposed adjacent to the body portion. A glass vial 1 has a conventional aerosol outlet 2 secured by means of a crimped cap 3. The vial 1 is formed of glass with an outer coating of polypropylene 6. The coating includes a clear or translucent portion defining at least one window 4 extending in an axial direction and in a circumferential direction across a distance that is less than a circumference of the vial 1 so that a level of the agent in the vial 1 is visible through the coating. The window 4 extending axially of the vial is formed by polishing a portion of the polypropylene coating so that the level of liquid within the vial 1 can be observed. As shown in FIGS. 1 and 2, the window 4 is at least partially disposed on the side wall 25 of the body portion 23. Gradations 5 allow a user to check whether the quantity of liquid available for dispensing is within predetermined maximum and minimum limits.

Figure 3:
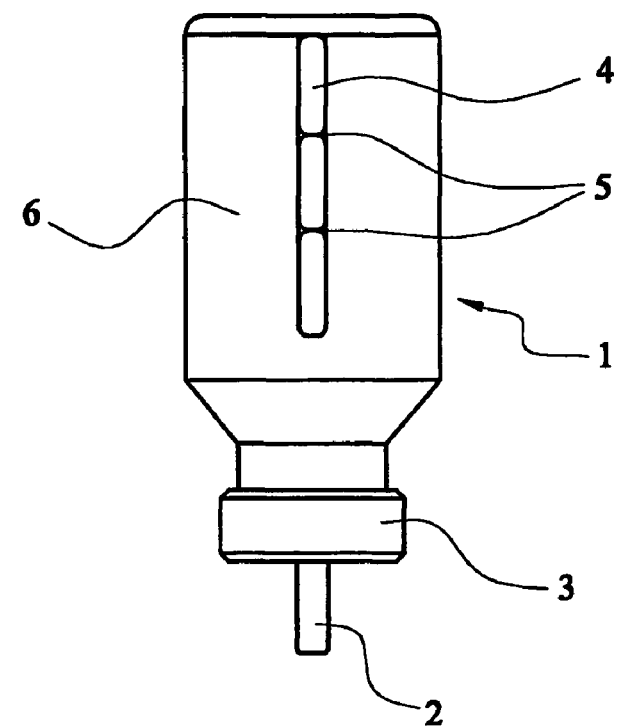
FIG. 3 shows the vial and a metered dose inhaler body.
Figure 3:
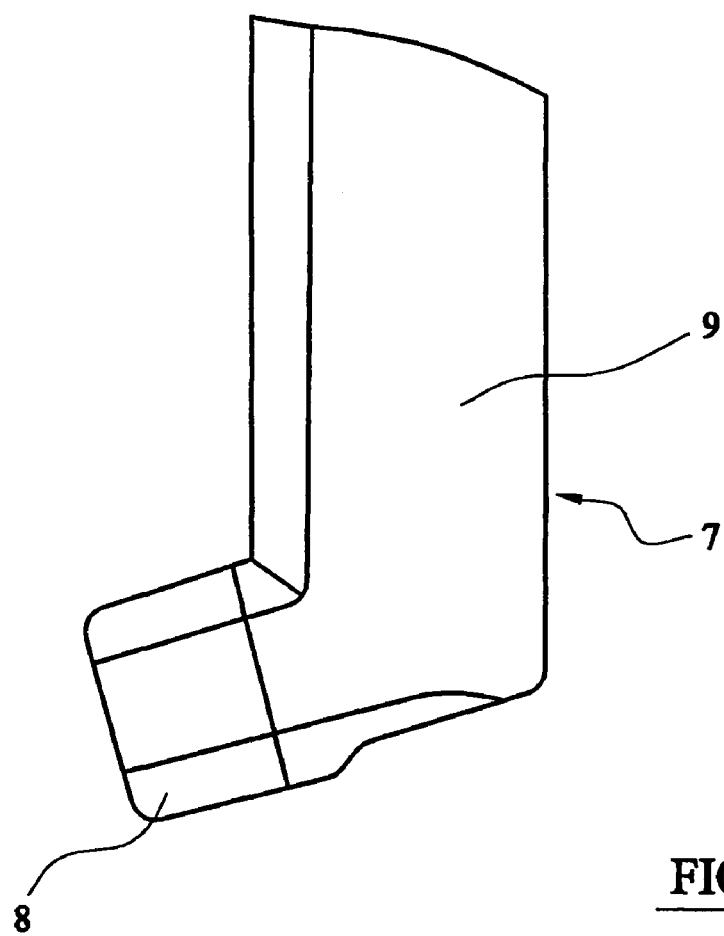

FIG. 3 shows the vial of FIGS. 1 and 2 inverted for insertion into a conventional metered dose inhaler body 7. The body 7 includes a nozzle 8 defining a mouthpiece 8. The portion 9 of the body 7 into which the vial 1 is inserted may be composed of transparent or translucent material so that the vial 1 can be observed without removal from the body 7.

Figure 4:
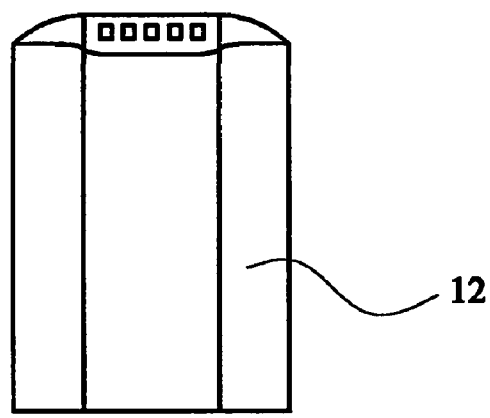
FIG. 4 shows the vial and an alternative metered dose inhaler body.
Figure 4:
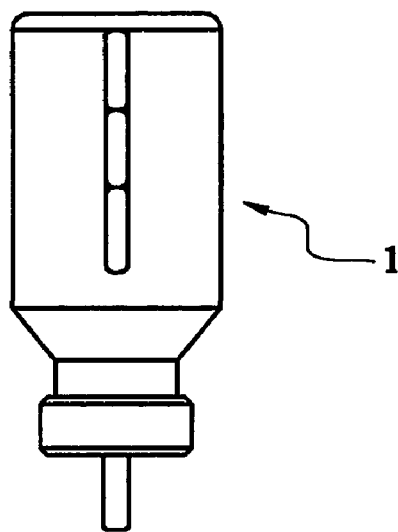
Figure 4:
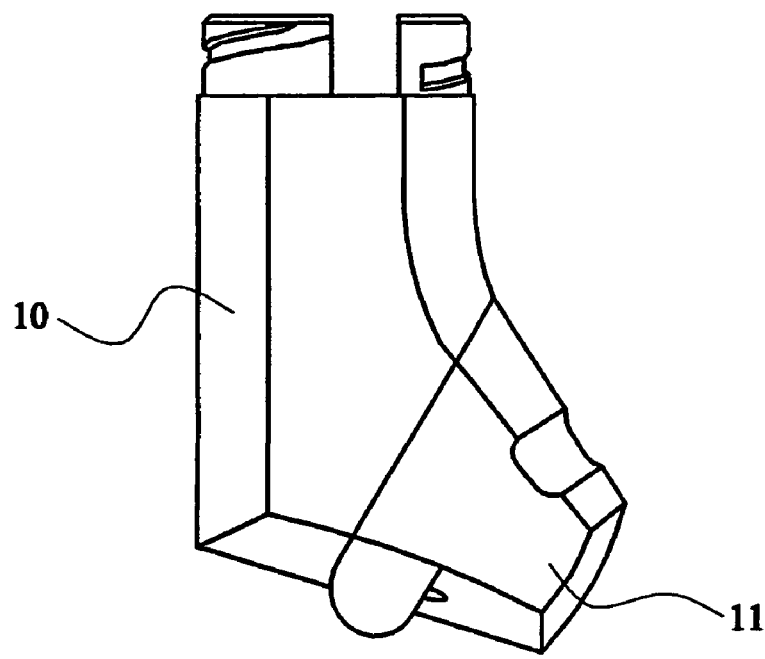

FIG. 4 illustrates the vial 1 inverted for insertion into a Norton EASI-BREATHE (Registered Trade Mark) metered dose inhaler. The inhaler comprises a body portion 10 adapted to receive the vial 1 and having a pivotable cap 11 which may be opened to facilitate dispensing of the drug. A cap 12 secured to the body 10 may be twisted to prime the metered dose inhaler mechanism (not shown).

In use, the cap 12 may be removed from the body 10 to allow inspection of the vial 1. Alternatively a window (not shown) may be provided in the side of the body 10 to facilitate inspection of the vial 1 without removal from the body 10.

Figure 5:
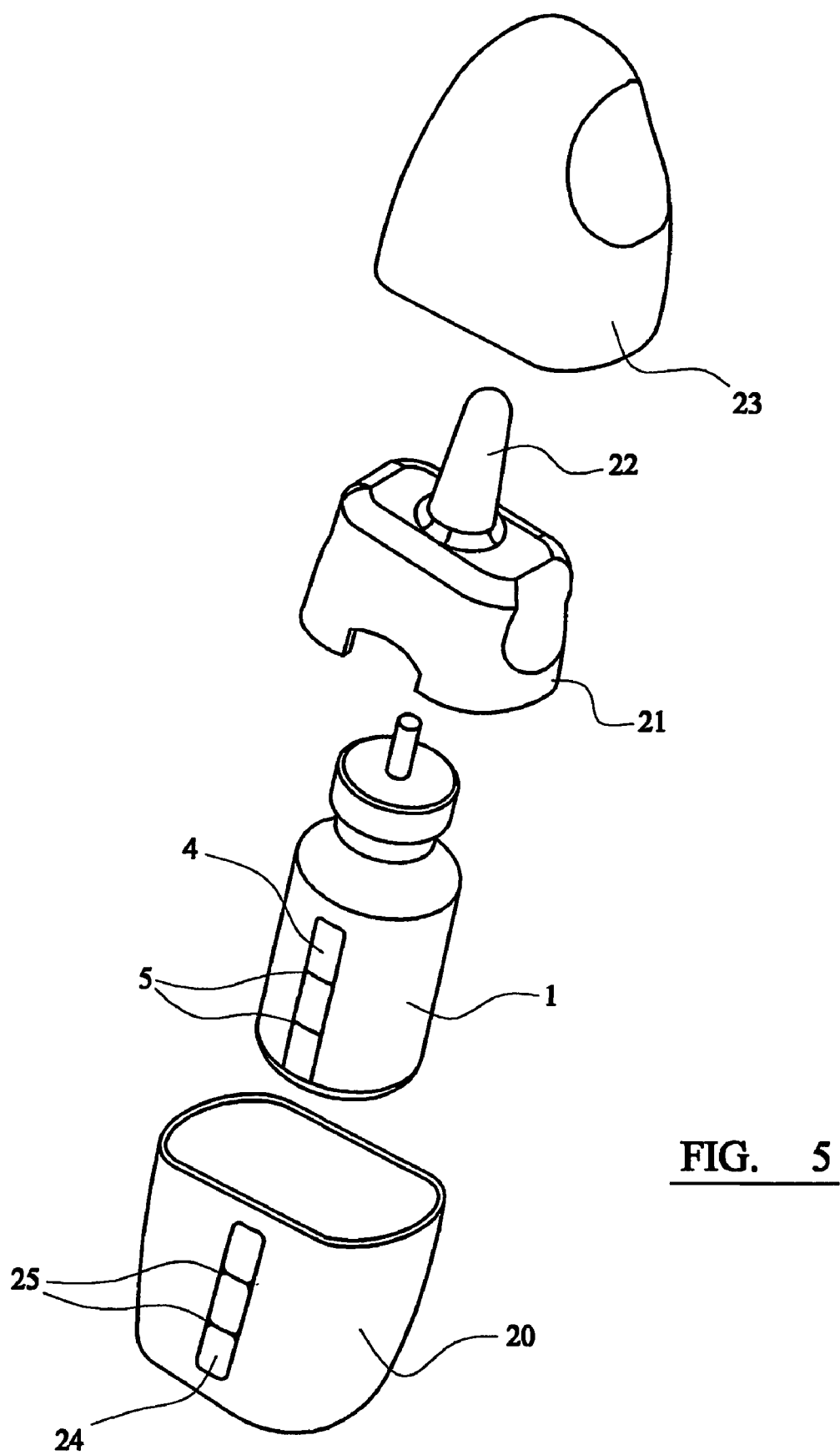
FIG. 5 shows the vial with a nasal spray dispenser.

FIG. 5 illustrates a nasal spray device in accordance with an embodiment of this invention. The vial 1 is engaged in a cap 21 having an outlet 22 for insertion into the nasal cavity. The base 20 into which the body of the vial 1 is received incorporates a window 24 having gradations 25. In use the window 4 is aligned with the window 24 so that the level of liquid within the vial 1 may be observed without removing the latter from the base 20.

In this embodiment, the gradations 5 are optional but may serve to confirm to a patient by alignment with the gradations 25 that the vial is correctly inserted into the spray cap 21 and base 20.

The invention claimed is:

1. A respiratory aid for use in self-administration of an agent for combating the symptoms of a respiratory disorder, said respiratory aid comprising:
   a container for the agent, the container including a transparent vial extending in an axial direction, the vial including a side wall having an outer surface coated with a coating of polymeric material, the coating including a clear or translucent portion defining at least one window extending in the axial direction and in a circumferential direction across a distance that is less than a circumference of the vial so that a level of the agent in the container is visible through the coating;
   a discharge valve and a nozzle operatively connected to the container and through which an amount of the agent may be dispensed from the container; and
   an actuator body adapted to actuate the discharge valve, wherein the actuator body includes a side wall defining a window, wherein the window of the actuator body is aligned with the window of the container so that the level of the agent in the container is visible through the window of the actuator body.

2. A respiratory aid as claimed in claim 1, wherein the actuator body is adapted to administer a therapeutically or preventatively effective amount of the agent into the respiratory passages of a subject through a delivery outlet.

3. A respiratory aid as claimed in either of claim 1 or 2, wherein the coating of polymeric material is composed of a polymer selected from the group consisting of a polyolefin, ABS, acetyl based polymers and acrylic based polymers.

4. A respiratory aid as claimed in claim 3 wherein the polyolefin is selected from the group consisting of polyethylene, polypropylene, polystyrene and copolymers or blends thereof.

5. A respiratory aid as claimed in claim 3 wherein the polyolefin is polypropylene.

6. A respiratory aid as claimed in claim 1, further comprising a second clear or translucent window in the coating of polymeric material, the second window being on an opposite side of the transparent vial from the at least one window of the container.

7. A respiratory aid as claimed in claim 1 being an inhaler or nasal spray device.

8. A respiratory aid as claimed in claim 1 being a metered dose inhaler.

9. A respiratory aid as claimed in claim 1, wherein the nozzle is an aerosol delivery outlet secured to the container by a crimped cap.

10. A respiratory aid as claimed in claim 1 wherein the vial is at least partially inserted into at least a part of the actuator body.

11. A respiratory aid as claimed in claim 1, wherein the actuator body comprises:
   a cover into which a nozzle end of the container is inserted, the cover having a delivery outlet for insertion into the nasal cavity of a subject; and
   a base into which an end of the container opposite the nozzle end is inserted, the base incorporating the window of the actuator body so that the level of the agent in the container is visible through the actuator body.

12. A respiratory aid as claimed in claim 11, wherein the base incorporates gradations for indicating the number of doses of the agent in the container.

13. A respiratory aid as claimed in claim 1, wherein the actuator body comprises:
   a cover into which a nozzle end of the container is inserted, the cover having a delivery outlet for insertion into the mouth of a subject, whereby the window of the container is exposed through the window of the actuator body without dislocation or removal of the cover.

14. A respiratory aid as claimed in claim 1, wherein the actuator body comprises:
   a cover into which a nozzle end of the container is inserted, the cover having a delivery outlet for insertion into the mouth of a subject; and a base into which an end of the container opposite the nozzle end is inserted, the base incorporating the window of the actuator body to so that the level of the agent in the container is visible through the actuator body.

15. A respiratory aid as claimed in claim 1, wherein the actuator body comprises:
a cover into which a nozzle end of the container is inserted, the cover having a delivery outlet for insertion into the mouth of a subject; and
a base into which an end of the container opposite the nozzle end is inserted, the base being detachable from the cover to permit inspection of the level of the agent in the container.

16. A respiratory aid as claimed in any of claims 13 to 15 wherein the discharge valve is a metered discharge valve.

17. A respiratory aid as claimed in claim 13 wherein the cover is capped with a pivotal cap.

18. A respiratory aid as claimed in either of claim 14 or 15, wherein the discharge valve is a metered discharge valve, and the base is rotatable to prime the metered discharge valve.

19. A respiratory aid as claimed in claim 1, further comprising an amount of the agent disposed in the container, the agent being present in a formulation with a propellant.

20. A respiratory aid as claimed in claim 1 further comprising indicia adjacent the window of the container and/or the actuator body for indicating a number of doses of the agent in the container.

21. A medical aerosol device, comprising:
a container including a transparent vial extending in an axial direction, the transparent vial having an outer surface coated with a layer of polymeric material defining at least one clear or translucent portion extending in the axial direction and in a circumferential direction across a distance that is less than a circumference of the vial, the clear or translucent portion arranged so that a level of fluid in the container is visible through the layer of polymeric material;
a discharge valve and a nozzle through which fluid may be dispensed from the container; and
an actuator extending in an axial direction adapted to actuate the discharge valve, wherein the actuator includes a side wall defining a window extending in the axial direction, wherein the window of the actuator is aligned with the window of the container so that the level of the agent in the container is visible through the window of the actuator.

22. A respiratory aid as claimed in claim 1, wherein the actuator body includes a base adapted to receive the vial, the base incorporating the window of the actuator body so that the level of the agent in the container is visible through the actuator body.

23. A respiratory aid as claimed in claim 22, wherein the base includes gradations for indicating the number of doses of the agent in the container.

24. A respiratory aid as claimed in claim 22, wherein in use the window in the base is aligned with the window in the coating of polymeric material on the vial so that the level of the agent in the container is visible through the actuator body.

25. A medical aerosol device as claimed in claim 21, wherein the actuator includes a base adapted to receive the vial, the base incorporating the window of the actuator so that the level of fluid in the container is visible through the actuator.

26. A medical aerosol device as claimed in claim 25, wherein the base includes gradations for indicating the number of doses of fluid in the container.

27. A medical aerosol device as claimed in claim 25, wherein in use the window in the base is aligned with the at least one clear or translucent portion in the layer of polymeric material on the vial so that the level of fluid in the container is visible through the actuator.

28. A medical aerosol device as claimed in claim 21 further comprising indicia adjacent the clear or translucent portion of the container for indicating a number of doses of fluid in the container.

29. A respiratory aid for use in self-administration of an agent for combating the symptoms of a respiratory order, said respiratory aid comprising:
a container for the agent, the container including a transparent vial extending in an axial direction, the vial having an outer surface coated with a coating of polymeric material defining at least one clear or translucent window extending in the axial direction and in a circumferential direction across a distance that is less than a circumference of the vial so that a level of the agent in the container is visible through the coating;
a discharge valve and a nozzle operatively connected to the container and through which an amount of the agent may be dispensed from the container; and
an actuator body adapted to actuate the discharge valve, the actuator body including a base adapted to receive the vial, the base including a side wall defining a window, wherein the window of the base is aligned with the window of the container so that the level of the agent in the container is visible through the window of the actuator body.

30. A respiratory aid as claimed in claim 29, wherein the base includes gradations for indicating a number of doses of the agent in the container.

31. A respiratory aid as claimed in claim 29, wherein in use the window in the base is aligned with the window in the coating of polymeric material on the vial so that the level of the agent in the container is visible through the actuator body.

32. A respiratory aid for use in self-administration of an agent for combating the symptoms of a respiratory disorder, said respiratory aid comprising:
a container for the agent, the container including a transparent vial extending in an axial direction, the vial having an outer surface coated with a coating of polymeric material, the coating including a clear or translucent portion surrounded by an opaque portion to define at least one window extending in the axial direction and in a circumferential direction across a distance that is less than a circumference of the vial so that a level of the agent in the container is visible through the coating;
a discharge valve and a nozzle operatively connected to the container and through which an amount of the agent may be dispensed from the container; and
an actuator body adapted to actuate the discharge valve, wherein the actuator body includes a side wall defining a window, wherein the window of the actuator body is aligned with the window of the container so that the level of the agent in the container is visible through the window of the actuator body.

33. A respiratory aid as claimed in claim 32 further comprising indicia adjacent the window of the container and/or the actuator body for indicating a number of doses of the agent in the container.

* * * * *